United States Patent [19]

Potter

[11] 4,159,638

[45] Jul. 3, 1979

[54] THERMISTOR DETECTOR CIRCUIT AND DISCRIMINATING NETWORK FOR HEAT ABSORPTIVE MEDIA

[76] Inventor: Bronson M. Potter, R.F.D. 1, Greenville, N.H. 03048

[21] Appl. No.: 825,670

[22] Filed: Aug. 18, 1977

Related U.S. Application Data

[63] Continuation-in-part of Ser. No. 752,199, Dec. 20, 1976, Pat. No. 4,116,045, and a continuation-in-part of Ser. No. 785,347, Apr. 7, 1977.

[51] Int. Cl.² .................. G01N 25/18; G01F 1/00; G01W 1/00
[52] U.S. Cl. .................. 73/61.1 R; 73/188; 73/204
[58] Field of Search .................. 73/61.1 R, 53, 188, 73/204, 27 R

[56] References Cited

U.S. PATENT DOCUMENTS

| 2,437,449 | 3/1948 | Ames, Jr. et al. | 73/204 UX |
| 2,650,496 | 9/1953 | Middleton et al. | 73/204 |
| 3,429,178 | 2/1969 | Durbin | 73/204 UX |
| 3,548,637 | 12/1970 | Wicks | 73/204 X |
| 3,852,997 | 12/1974 | Horvath | 73/61.1 R |

FOREIGN PATENT DOCUMENTS 826780  11/1969  Canada .................. 73/27 R Primary Examiner—Richard C. Queisser
Assistant Examiner—Joseph W. Roskos

[57] ABSTRACT

Detecting conditions related to the heat absorptive characteristics of a surrounding medium by heated thermistors exposed for heat transfer to the medium, and connected to a restorative energizing electronic circuit that supplies heating power. The restorative circuit responds to differences between the resistance of the sensing leg containing the thermistors and a reference value to vary the power flow through the leg and thus to restore the resistance of the leg toward the reference value. With two or more thermistors in the leg, the thermistors are heated in unison by the single energizing circuit, each thermistor is disposed in a different relationship to the conditions to be discriminated and differences between the individual thermistor resistances, reflecting differing rates of heat loss to the medium provide indications of the various conditions. When one thermistor is used, the power flow through the overall leg can serve as a measure of conditions of the surrounding medium. Features of the invention employing two thermistors include positioning one thermistor for contact with water and the other thermistor above the oil/water interface to detect a layer of oil if present and using the two thermistors as a fluid flow detector with temperature compensation. Unique circuit arrangements are shown that achieve effective thermistor action with an economy of parts and energizing power.

20 Claims, 7 Drawing Figures

THERMISTOR DETECTOR CIRCUIT AND DISCRIMINATING NETWORK FOR HEAT ABSORPTIVE MEDIA

This application is a continuation-in-part of my co-pending U.S. patent applications Ser. No. 752,199 filed Dec. 20, 1976, entitled "Oil Detector" now U.S. Pat. No. 4,116,045 and Ser. No. 785,347 filed Apr. 7, 1977, entitled "Detector and Control", hereby incorporated by reference.

This invention relates to devices which respond to a heat absorptive characteristic condition of a surrounding medium and to devices for discriminating at least one condition from a set of different conditions that are related to the heat absorptive properties of the medium. The conditions may relate to thermal conductivity, fluid motion, temperature, etc., for purposes such as detecting oil spills on water or determining the flow condition or identity of a fluid.

The purpose of the invention is to provide detection devices that are simple, durable, and can be made at low cost. Another purpose is to enable the various factors affecting heat transfer into a medium to be discriminated from one another, to eliminate spurious conditions, such as temperature changes, to achieve devices that are extremely sensitive. A further object is to enable fluids that are difficult to discriminate, from water for example, to be reliably detected.

According to the invention, the device which accomplishes these objects comprises an electrical sensing leg having at least one thermistor exposed to a surrounding heat absorptive medium and connected to a restorative energizing electronic circuit supplying heating power to the leg to restore its resistance toward a predetermined reference value. Maintaining the resistance of the sensing leg near the reference value assures that the resistance, and hence temperatures, of the individual thermistors remain within their designed operating ranges, eliminating the possibility of burning out one or more thermistors or igniting a volatile fluid, if present; because the restorative circuit, powered preferably by a single, direct current source, energizes the sensory leg as a whole, any thermistor in the leg is affected as the direct current flow through the leg is controlled in response to changing conditions of the surrounding medium. Also when more than one thermistor is located in a single sensing leg, noise inherent in any active electronic circuit influences the whole set of thermistors equally, allowing the effects of such noise to be eliminated.

In embodiments of the invention in which the sensing leg comprises a single thermistor, the power required to maintain the thermistor resistance equal to a reference resistance is a measure of the thermal loss of the thermistor to the medium. An output signal representing this power is therefore a measure of the heat absorptive characteristics of the medium, and may be used, for example, to identify an unknown fluid or to distinguish between an unknown fluid and water.

In embodiments employing multiple thermistors, similarly useful information is derived from the differential change in resistance between the various thermistors in the leg, made possible by the common means of applying power to the leg.

In preferred embodiments of the invention for discrimination among a number of conditions affecting heat flow into a medium, the sensing leg comprises an electrical network that includes a set of thermistors corresponding to the number of conditions to be descriminated. Each of the thermistors is disposed in a different heat transfer relationship with the medium and means are provided to derive an output signal, dependent upon the resistance values of the individual thermistors, indicating the condition to be sensed. As a detector, therefore, a device embodying the invention provides information about the rate of heat loss to a surrounding medium due to a single condition of interest, eliminating the effects of other conditions, e.g., temperature fluctuations.

In a specific preferred embodiment the electrical network of thermistors comprises one leg of a resistance comparing bridge. Whenever the resistance of the network differs from a reference resistance in another leg of the bridge, the restorative circuit varies the power flow through the network, bringing the bridge into balance.

In preferred embodiments the electrical network itself comprises an ancillary bridge including two thermistors and two resistors of equal value comprising a voltage divider, allowing the resistances of the two thermistors to be compared. Any difference in resistance between the thermistors produces a voltage across the ancillary bridge which serves as an output signal and indicates the condition of interest. The two thermistors may be connected in series or parallel within the ancillary bridge for this purpose.

In another preferred embodiment the sensing leg or the electrical network of multiple thermistors is connected in series with a temperature-independent reference resistor in an electronic energizing circuit. Because of the series connection, the same current flows through the reference resistor and the network. Connected across the reference resistor and across the network are the inputs to separate operational amplifier means whose outputs are measures of the voltage across the reference resistor and the network and are also measures of the respective resistance values. A further operational amplifier means is disposed in the circuit so that its input is the difference between the outputs of the operational amplifier means whose inputs are connected across the network and reference resistor. The output of this further operational amplifier means is proportional to the difference in resistance between the series network and the reference resistor, and is used to regulate the power flow through the network in a manner tending to maintain the resistance of the network equal to the resistance value of the reference resistor.

Another preferred embodiment of the invention is a detector for sensing a difference between an unknown fluid, e.g., oil, and water. In this embodiment, the electrical network whose resistance is maintained relative to the predetermined value includes two thermistors, one a sensor and the other a reference, incorporated into a probe for positioning the sensing thermistor at a level for heat transfer contact with the fluid, if present, and the reference thermistor at a level for heat transfer contact with water only. When the water surface is contaminated by a fluid whose viscosity is lower than that of water, such as high petroleum distillates, the heating effect of the sensing thermistor upon the unknown fluid is less than when water alone is present, thereby allowing reduced convection heat loss to improve the accuracy of detection of the unknown fluid.

In another embodiment, a first thermistor in a sensing leg network serves as a sensor for a condition to be sensed and a second thermistor in the network constitutes a temperature compensator, exposed to the same temperature as the first thermistor but not exposed to the condition to be sensed. Here again the resistance of the overall network is compared and maintained with reference to the predetermined value. One such embodiment is a fluid flow detector. In this case, the reference thermistor is exposed for contact with a still fluid at the same temperature as the fluid whose flow is to be sensed, and the sensing thermistor is exposed to the flowing fluid itself. In a similar embodiment used as a fluid immersion or level detector, the reference thermistor is exposed constantly to air or liquid and the sensing thermistor is exposed for contact with liquid upon immersion.

Preferred embodiments of the invention for these various applications feature a resistance comparator signalling the difference between the present value of the resistance of the sensing leg and a temperature independent reference, and a power regulator responsive to the comparator to vary the power flow through the sensing leg to reduce the resistance difference. In one such embodiment the resistance comparator preferably comprises at least one reference resistor and a transistor means connected so that the signal on an output lead of the transistor means represents the resistance difference. The power regulator preferably comprises a transistor means operative as a series regulator connected between a single, direct current energy source and the sensing leg. The output lead of the resistance comparator is connected to the effective base of the power regulator transistor means, thereby controlling the flow of power through the sensing leg.

In a specific preferred embodiment the thermistor sensing leg and a plurality of resistors comprise a bridge connected to a resistance comparator transistor means to signal the degree of unbalance of the bridge attributable to the difference between the present resistance value of the sensing leg and the predetermined reference value. Specifically, the bridge comprises a first resistor having a resistance value equal to the predetermined reference value, and a pair of series-connected resistors of equal value comprising a divider. The divider forms one path from the power regulator to ground and the first resistor, connected in series with the sensing leg, forms a second path from the power regulator to the ground. The resistance comparator transistor means has its base effectively connected to the mid-point of the divider, and its emitter effectively connected between the first resistor and sensing leg. Its effective collector is connected to control the power regulator.

In a still further embodiment of the invention herein, the restorative circuit consists of a constant current circuit having two parallel branches, one branch containing the sensing leg and the other connected through the collector and emitter of a transistor means; the base of the transistor means connected in a feedback relation to respond to the voltage change across the sensing leg and thereby driving the resistance of the sensing leg toward the reference resistance.

Another embodiment of the invention is a wind direction indicator comprising three thermistors disposed, for example, about the periphery of a cylinder and exposed to the wind. As the wind direction shifts, the rates of heat loss from the thermistors will change, their differing resistances allowing the wind direction to be inferred.

In all of the foregoing embodiments circuitry is provided to heat the network of thermistors, as needed, sufficiently to clean the thermistors of any residues, e.g., oil films, that may have coated the thermistors, allowing subsequent operation after having once been exposed to and coated by oil or other fluids. Means for accomplishing this are shown in my copending application, Ser. No. 752,199, referred to above, incorporated herein by reference.

The embodiments and features of the invention herein will be further understood in conjunction with the following drawings in which.

DESCRIPTION OF PARTICULAR EMBODIMENTS

Figure 1:
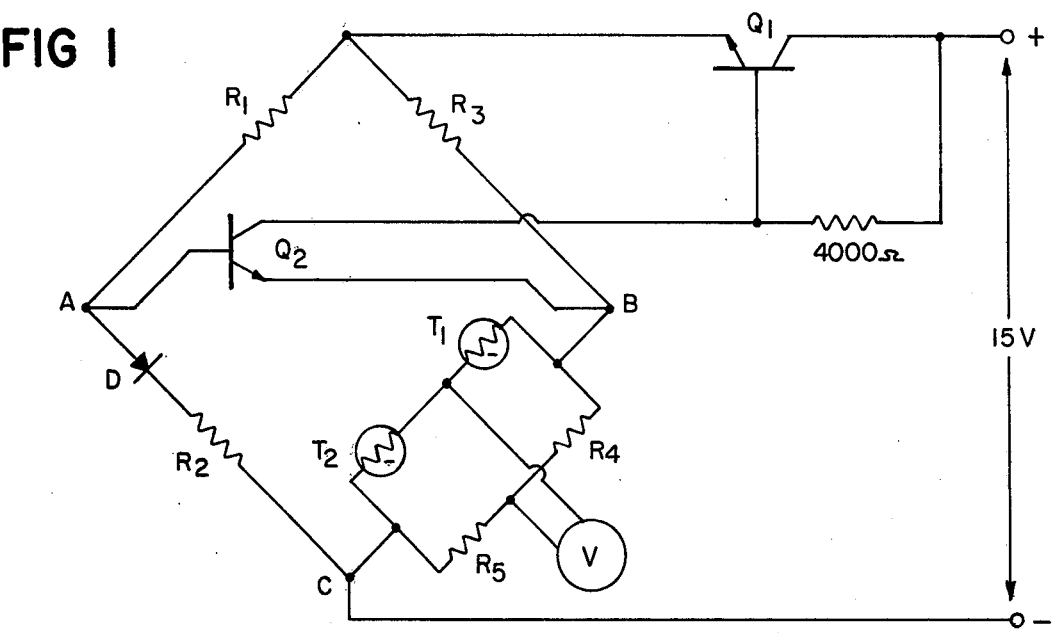
FIG. 1 is a schematic diagram of the circuitry of a preferred embodiment according to the invention employing a series connection of two thermistors.

Referring to FIG. 1, transistor $Q_1$, a five-watt silicon transistor with $\beta$ over 100, operates as a standard series regulator. Transistor $Q_2$, a standard NPN entertainment transistor with $\beta$ over 100, serves to modify transistor $Q_1$'s base current in response to the current flow between the base and emitter of transistor $Q_2$ caused in turn by a resistance imbalance in the resistance comparing bridge circuit shown. Two arms of this bridge are formed by 1000Ω resistors $R_1$ and $R_2$; the other arms are formed by a 190Ω reference resistor $R_3$ and ancillary bridge comprising the series connections of the two thermistors $T_1$ and $T_2$ in parallel with series-connected resistors $R_4$ and $R_5$. Thermistors $T_1$ and $T_2$, both Fenwal GD31SM2, have negative temperature coefficients. Resistors $R_4$ and $R_5$ are each 1000Ω. The base and emitter of transistor $Q_2$ are connected to the midpoints of the resistance comparing bridge circuit. The diode D is a standard milliwatt device which compensates for the forward potential between the base and emitter of transistor $Q_2$. At 25° C. ambient temperature conditions, the thermistors $T_1$ and $T_2$ each have a resistance of 1000Ω.

In operation, whenever the resistance comparing bridge of FIG. 1 is unbalanced, a potential difference developes between points A and B. When the resistance of the ancillary bridge is higher than the reference resistor, transistor $Q_2$ is turned off allowing transistor $Q_1$ to be fully one. Power, therefore, flows through the ancillary bridge to ground causing heating of the thermistors and an attendent decrease in their resistance values. Power will continue to flow until the resistances of thermistors $T_1$ and $T_2$ change, thereby reducing the potential difference between A and B and bringing the bridge into balance. Transistor $Q_2$ then begins to turn on, robbing transistor $Q_1$ of some of its base current, thereby turning it partly off. As transistor $Q_1$ progressively turns off the current flow through the ancillary bridge is reduced. Thus, this restorative electronic circuit attempts to maintain the resistance of the ancillary bridge, consisting of the series-connected thermistors and resistors $R_4$ and $R_5$, equal to the resistance of the reference resistor $R_3$ in the face of changing conditions in the surrounding medium.

Whenever thermistors $T_1$ and $T_2$ are exposed to a surrounding medium such that the rate of heat loss from each of the thermistors is the same, the ancillary bridge $R_4$ and $R_5$ will be balanced; the voltage as measured by voltmeter V will be zero. If, for example, the temperature of the surrounding medium were to change, the resistance values of thermistors $T_1$ and $T_2$ will change. The resistance comparing bridge will then become unbalanced and the restorative electronic circuit will adjust the power flow through the ancillary bridge to restore balance. The output voltmeter V will continue to read zero, however, since the temperature of thermistor $T_1$ remains equal to the temperature of thermistor $T_2$, even though the flow of power through the thermistors will have changed. Temperature compensation has been achieved very simply by putting the two thermistors in the same arm of the main bridge circuit. When, however, the temperatures of thermistors $T_1$ and $T_2$ differ, as, for example, when one thermistor is exposed to a still fluid and the other to the same fluid in motion, the ancillary bridge becomes unbalanced and a voltage will register on voltmeter V indicating the velocity of the fluid in motion.

Figure 2:
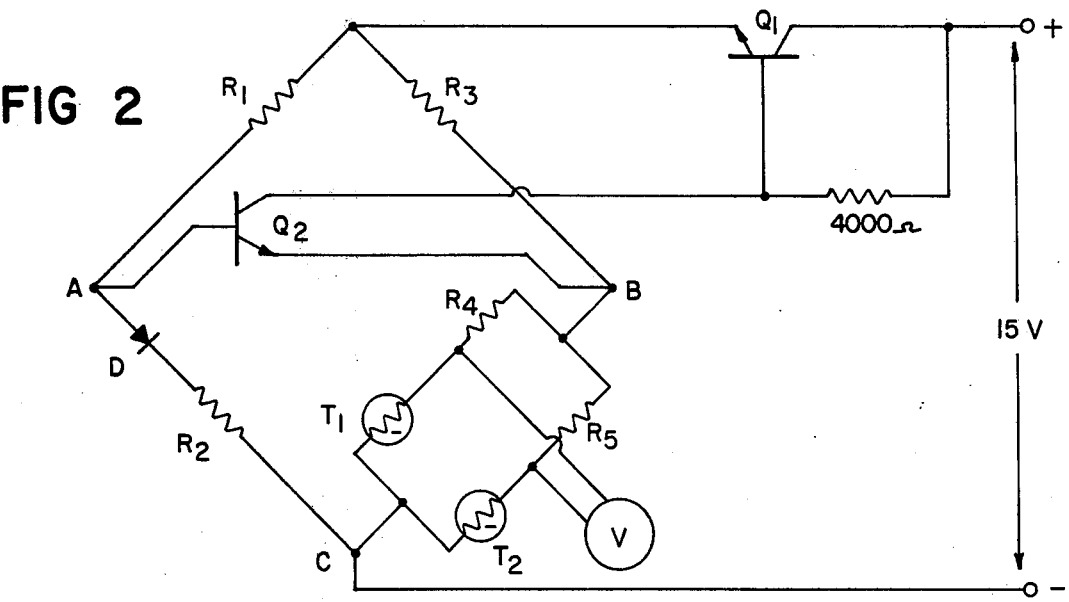
FIG. 2 is a schematic diagram, similar to FIG. 1, of an embodiment of the invention employing a parallel connection of two thermistors.

In the similar embodiment shown in FIG. 2, thermistors $T_1$ and $T_2$ are connected in parallel within the ancillary bridge having arms $T_1$, $T_2$, $R_4$ and $R_5$. Its operation is similar to the embodiment of FIG. 1. Only when the temperatures of thermistors $T_1$ and $T_2$ differ will voltmeter V register.

Figure 3A:
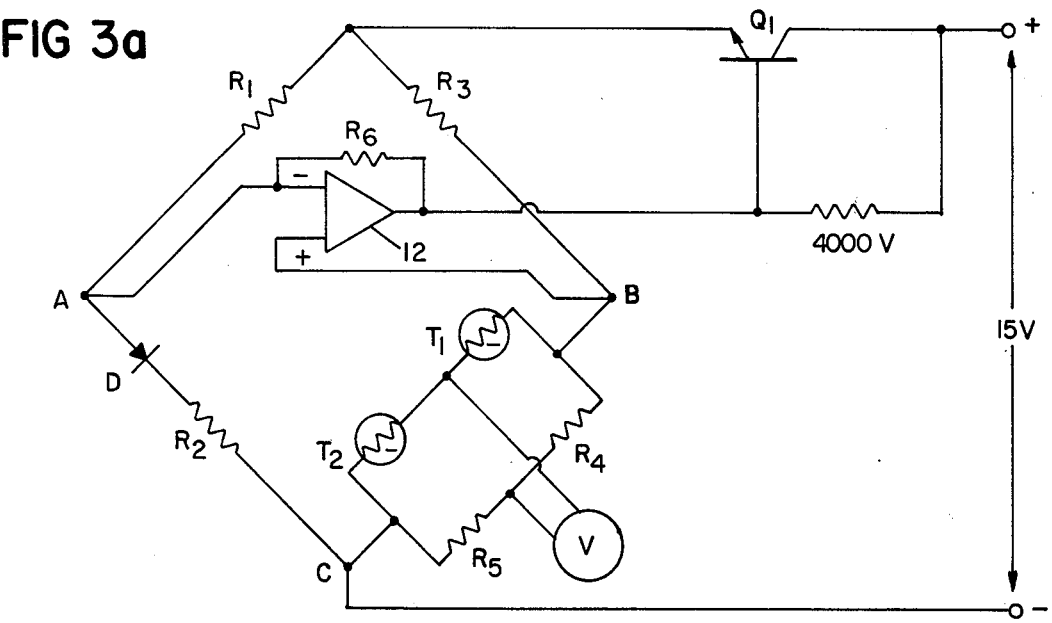
FIG. 3a is a schematic diagram of circuitry of an embodiment of the invention employing one operational amplifier.
Figure 3:
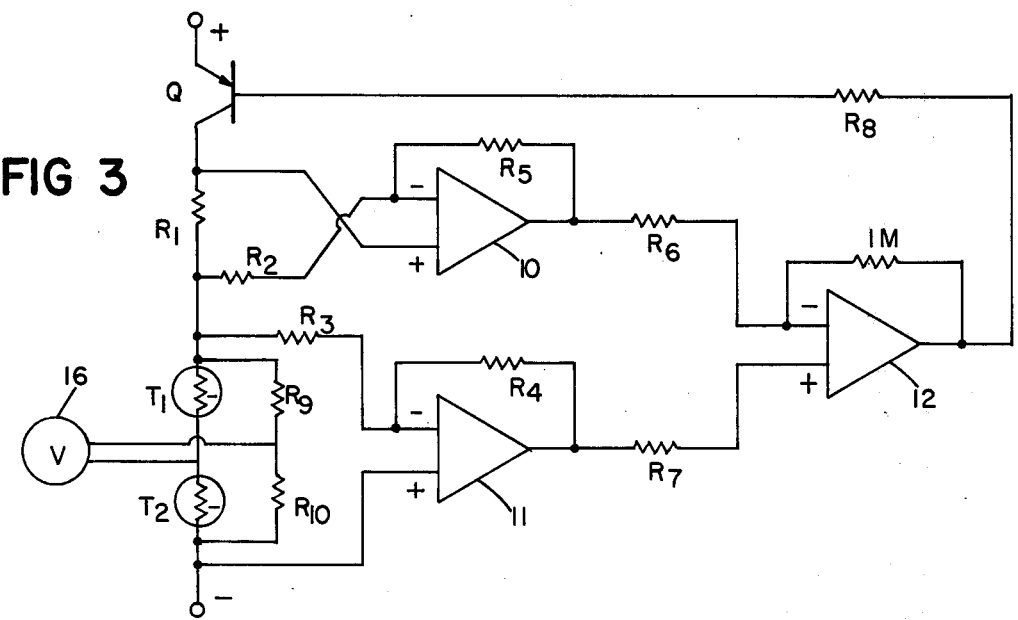
FIG. 3 is a schematic diagram of circuitry of an embodiment of the invention employing operational amplifiers.

FIG. 3 is an embodiment of the invention embodying operational amplifiers. Operational amplifier 10 is connected across reference resistor $R_1$ and serves as a gain of one inverter amplifier, with its output proportional to the voltage across resistor $R_1$. Operational amplifier 11 is connected across the ancillary bridge having arms $T_1$, $T_2$, $R_9$ and $R_{10}$ and serves as a gain of one amplifier with its output proportional to the voltage across the ancillary bridge. The two outputs are electrically subtracted and the difference serves as the input to operational amplifier 12, which serves as a gain of ten summing amplifier, with its output proportional to the difference in the voltages across the ancillary bridge and reference resistor $R_1$. Because the current flow through the ancillary bridge equals that through reference resistor $R_1$, the output of operational amplifier 12 is proportional to the difference in resistance between the ancillary bridge and reference resistor $R_1$. The output signal from operational amplifier 12 is connected to the base of transistor Q thereby controlling the flow of power through the ancillary bridge and controlling its resistance. Voltmeter 16 is connected across the ancillary bridge to indicate the difference in resistance between thermistors $T_1$ and $T_2$.

In this embodiment the frequency compensation and power supply connections to the operational amplifiers (routine to the art) are not shown. The following components are used:

| Thermistors $T_1$ and $T_2$ | Fenwal GD25SM2 |
|---|---|

| -continued | |
|---|---|
| series regulator Q | 2N1038 |
| operational amplifiers 10,11,12 | 709 |
| resistances: | |
| $R_1$ | 33 KΩ |
| $R_2$ | 2.7K Ω |
| $R_3$ | 2.7K Ω |
| $R_4$ | 2.7K Ω |
| $R_5$ | 2.7K Ω |
| $R_6$ | 10 K Ω |
| $R_7$ | 10 K Ω |
| $R_8$ | 330 K Ω |
| $R_9$ | 1000 Ω |
| $R_{10}$ | 1000 Ω |

FIG. 3a shows an embodiment of the invention similar to FIG. 1 in which transistor $Q_2$ of FIG. 1 has been replaced by operational amplifier 12 whose output is a measure of the main bridge unbalance. This output controls the power flow through the sensing leg via transistor $Q_1$.

Figure 4:
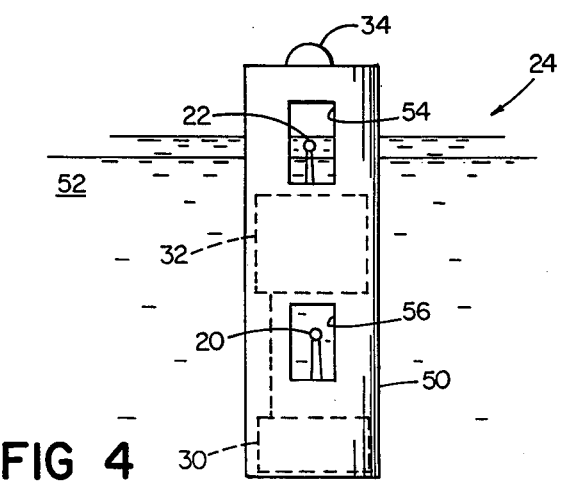
FIG. 4 is a diagrammatic view of an oil detection unit having two thermistors and employing the circuitry of FIG. 1 or FIG. 2.

FIG. 4 shows the invention embodied as an oil detection unit employing the circuit of FIG. 1 or 2. The oil detection system includes a buoyant, tubular housing 50 designed to float on water 52 to be monitored. Housing 50 has upper and lower recesses 54, 56. The buoyancy of housing 50 is such that recess 54 is disposed at the surface of the water and recess 56 is submerged. Reference thermistor 20 is disposed in recess 56 so that it remains under water. Sensing thermistor 22 is disposed in recess 54 at the air-liquid interface so that it is exposed to oil should a film of oil 24 exist on the monitored surface. The oil detection unit may be self-contained and include batteries 30 (which function as ballast), the electronic circuit of FIG. 1 or 2, 32, and an output indicator 34 on its upper surface. In another embodiment, the unit may be connected by flexible cable (not shown) to a remote power supply and to remote output indicator circuitry.

Figure 5:
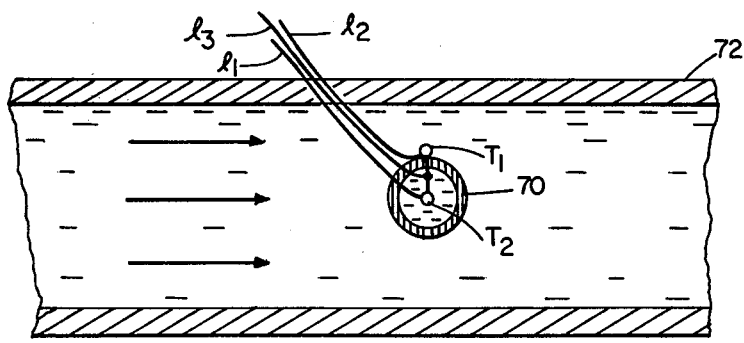
FIG. 5 is a diagrammatic view of an embodiment of the invention as a fluid flow detector.

Referring to FIG. 5, the invention is embodied as a fluid flow measuring device including a housing 70 enclosing a quantity of fluid at rest and a reference thermistor $T_2$ exposed to this fluid. On the outside of housing 70 is disposed sensing thermistor $T_1$. The whole unit is disposed within pipe 72 through which a fluid flows. The two thermistors are connected in the circuit of FIG. 1 or FIG. 2 by means of leads $l_1$, $l_2$, and $l_3$. When the fluid in pipe 72 is in motion, the rate of heat loss from thermistor $T_1$ is greater than the rate of heat loss from thermistor $T_2$ exposed to the reference fluid at rest. Therefore the ancillary bridge of FIG. 1 or FIG. 2 will become unbalanced, the resulting potential indicating the rate of fluid flow. As before, temperature compensation is achieved.

Figure 6:
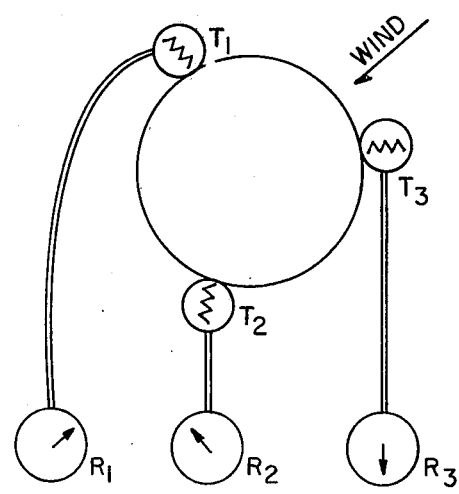
FIG. 6 is a diagrammatic view of an embodiment of the invention as a wind direction indicator.

FIG. 6 shows an embodiment of the invention employed as a wind direction indicator. Thermistors $T_1$, $T_2$ and $T_3$ are connected in series or parallel in a single sensing network, whose resistance is maintained relative to a predetermined value, e.g., by means of the restorative circuits of FIG. 1, FIG. 2 or FIG. 3. Resistance measuring meters $R_1$, $R_2$ and $R_3$ are connected across thermistors $T_1$, $T_2$ and $T_3$. The difference in the resistances of the thermistors as measured by the meters allow the wind direction to be determined. Alternatively the three outputs can be applied to three correspondingly arranged coils of a wind indicator drive motor, to position the wind indicator dial.

While the preferred devices used to perform the thermistor functions of this invention are those semiconductor units sold as "thermistors," it will be understood that certain features of the invention can be obtained using other devices, or combinations whose effects upon the circuit varies with temperature in a single valued relation. For instance, a temperature sensitive diode may be employed in certain instances, provided its temperature characteristic corresponds to the needs of the particular application involved.

What is claimed is:

1. A detector to discriminate at least one condition from a set of two or more different conditions of a heat absorptive medium that are related to heat transfer properties, comprising an electrical sensing network that includes a set of monitoring elements corresponding to the number of said conditions, each said element of said set disposed in a different relationship to said set of conditions and each said element having an electrical characteristic that changes as a single valued function of temperature, a restorative energizing circuit supplying heating power to said overall network, said circuit including reference means representing a predetermined desired value for the electrical characteristic of said overall network and responsive to change in the actual value of said characteristic of said overall network from said predetermined value to vary the flow of power to said network in the manner to restore said actual value of said characteristic of said overall network toward said predetermined value, and means to derive an output signal dependent upon the actual values of said characteristics of said individual elements and related to the thermal loss of each of said individual elements to said medium, and indicating said one condition.

2. The detector of claim 1 wherein said network comprises one leg of a bridge, said network connected to be driven toward balance in said bridge by said restorative energizing circuit.

3. The detector of claim 1 wherein said network comprises a bridge circuit including two monitoring elements and two references of equal value comprising a divider, and means to derive a signal from said bridge dependent upon the difference in said actual values of said characteristics of said elements.

4. The detector of claim 3 wherein said elements are connected in series within said bridge, said signal being the voltage across said bridge, between points respectively between said two elements and said two references.

5. The detector of claim 3 wherein said elements are connected in parallel within said bridge, said signal being the voltage across said bridge, between two points in the respective legs of said bridge, each point lying between one of said elements and its respective reference.

6. The detector of claim 1 adapted to detect liquid floating on water wherein a first of said elements is exposed at a first level for heat transfer contact with water and a second of said elements is exposed at a relatively higher level for heat transfer contact with said liquid when present.

7. An oil pollution detector constructed according to claim 1 wherein said elements and said circuitry are chosen to respond to the heat transfer characteristic differences between oil and water, one of said elements exposed to water subject to contamination by oil and the other exposed to water not subject to said contamination.

8. The detector constructed according to claim 1 wherein a first of said elements is a sensor for a condition of said heat absorptive medium to be sensed and a second said element constitutes a temperature compensator that is exposed to the same temperature as said first element and is not exposed to said condition to be sensed.

9. A fluid flow detector comprising the detector of claim 1 wherein said elements are exposed to fluids of similar chemistry at the same temperature, a first of said elements exposed to still fluid and a second of said elements exposed to fluid flow to be sensed.

10. The detector of claim 1 wherein said restorative energizing electronic circuit includes a comparator signalling the difference between the present value of said characteristic of said sensing network and a reference, and a power regulator responsive to said comparator to vary power flow through said sensing network to reduce said difference.

11. The detector of claim 10 powered by a single direct energy source, wherein said power regulator comprises a transistor means operative as a series regulator, connected between said single, direct current energy source and said sensing network.

12. The detector of claim 11 wherein said comparator comprises at least one reference and transistor means connected so that the signal on an output lead of said transistor means represents said difference, the effective base of said power regulator transistor means connected to said comparator output lead.

13. The detector of claim 12 wherein said sensing network and a plurality of references comprise a bridge, said transistor means connected to signal the degree of unbalance of said bridge attributable to the difference of the present value of said characteristic of said sensing network from said predetermined value.

14. The detector of claim 13 wherein said characteristic is resistance and said bridge comprises a first resistor having a resistance value equal to said predetermined value, and a pair of series connected resistors of equal value comprising a divider, said divider forming one path from said regulator to ground and said first resistor and said sensing network connected in series forming a second path from said regulator to ground, said transistor means having its base effectively connected to the midpoint of said divider and its effective emitter connected between said first resistor and said sensing network and its effective collector connected to control said power regulator.

15. The detector of claim 10 wherein said characteristic is resistance and said comparator comprises first, second and third operational amplifier means, the first connected so that its output represents the resistance value of a reference, the second connected so that its output represents the resistance of said network, and said third operational amplifier means having as inputs said outputs of said first and second operational amplifier means, and connected so that the output of said third operational amplifier means represents said difference between the present resistance value of said network and said reference.

16. The detector of claim 2 wherein said characteristic is resistance and said network comprises an ancillary bridge including two elements and two resistors of equal value, and means to derive a signal from said ancillary bridge dependent upon the difference in resistance of said thermistors.

17. The detector of claim 16 wherein said elements are connected in series within said ancillary bridge and said two resistors comprise a divider, said signal being the voltage across said ancillary bridge, between points respectively between said two elements and said two resistors.

18. The detector of claim 16 wherein each said element is connected in series with a said resistor and said series connected elements and resistors are connected in parallel within said ancillary bridge, said signal being the voltage across said ancillary bridge, between two points in the respective legs of said ancillary bridge, each point lying between one of said elements and its respective resistor.

19. The detector of claim 1 wherein said characteristic is resistance.

20. The detector of claim 3 wherein said characteristic is resistance.

* * * * *